United States Patent [19]
Miyahara et al.

[11] Patent Number: 5,814,321
[45] Date of Patent: Sep. 29, 1998

[54] OIL ADJUVANT VACCINE AND METHOD FOR PREPARING SAME

[75] Inventors: Tokuji Miyahara; Kozo Takase, both of Kumamoto-ken; Koichi Saito, Amagasaki; Yoko Kishimoto, Akashi; Satoru Tokuyama, Nishinomiya, all of Japan

[73] Assignees: Juridical Foundation The Chemo-Sero-Therapeutic Research Institute, Kumamoto; NOF Corporation, Tokyo, both of Japan

[21] Appl. No.: 758,374

[22] Filed: Nov. 29, 1996

[30]    Foreign Application Priority Data

Nov. 30, 1995  [JP]  Japan ..................................... 7-311964
Nov. 30, 1995  [JP]  Japan ..................................... 7-311965

[51] Int. Cl.$^6$ ........................... A61K 45/00; A61K 9/107
[52] U.S. Cl. ..................................... 424/278.1; 424/283.1; 514/937; 514/938; 514/939; 514/943
[58] Field of Search .............................. 424/278.1, 283.1; 514/937, 938, 939, 943

[56]               References Cited
             U.S. PATENT DOCUMENTS

| | | | |
|---|---|---|---|
| 4,125,603 | 11/1978 | Audibert et al. | 424/278.1 |
| 4,647,586 | 3/1987 | Mizushima et al. | 514/532 |
| 4,933,179 | 6/1990 | Allison et al. | 514/2 |
| 4,985,173 | 1/1991 | Takahashi et al. | 514/938 |
| 5,422,109 | 6/1995 | Brancq et al. | 424/278.1 |
| 5,444,041 | 8/1995 | Owen et al. | 514/2 |

FOREIGN PATENT DOCUMENTS

| | | |
|---|---|---|
| 6-39386 | 5/1994 | Japan . |
| 6-172216 | 6/1994 | Japan . |
| 6-81731 | 10/1994 | Japan . |
| 7-509733 | 10/1995 | Japan . |
| WO 91/00107 | 1/1991 | WIPO . |

OTHER PUBLICATIONS

Journal of the Society of Cosmetic Chemists, pp. 311–326, William C. Griffin, "Classification of Surface–Active Agents By 'HLB'".

*Primary Examiner*—Michael P. Woodward
*Attorney, Agent, or Firm*—Oblon, Spivak, McClelland, Maier & Neustadt, P.C.

[57]                ABSTRACT

A water-in-oil type oil adjuvant vaccine comprises 20 to 90% by weight of an oil phase A) which is in a liquid state at ordinary temperature; 0.5 to 30% by weight of an emulsifying agent comprising a non-ionic surfactant B) which is a partial ester derived from a polyhydric alcohol carrying at least three hydroxyl groups and a fatty acid and which is in a liquid state at 40° C. and a polyoxyethylene (20 to 60 moles) hydroxy fatty acid triglyceride C); and 5 to 75% by weight of an aqueous phase D) containing a biologically acceptable and effective amount of antigens, and optionally E) 0.01 to 10% by weight of an amino acid or a salt thereof and 0.01 to 10% by weight of a non-reducing sugar or a sugar alcohol having at least 5 hydroxyl groups in the molecule. In addition, a water-in-oil-in-water type oil adjuvant vaccine comprises the foregoing water-in-oil type oil adjuvant vaccine as an internal phase and an outer aqueous phase F) comprising 0.2 to 20% by weight of an emulsifying agent which comprises a non-ionic surfactant and which has an overall HLB value of not less than 10. The oil adjuvant vaccines show a high ability to induce an antibody-production over a long period of time and are excellent in requirements for medicines such as stability and safety.

9 Claims, No Drawings

OIL ADJUVANT VACCINE AND METHOD FOR PREPARING SAME

BACKGROUND OF THE INVENTION

1. Field of the Invention

The present invention relates to an oil adjuvant vaccine as well as a method for preparing the vaccine.

2. Prior Art

The oil adjuvant vaccine has been well-known for long as a vaccine for effectively potentiating immunity. Experimentally, there has still been used the Freund's adjuvant as a classic oil adjuvant vaccine since it has a quite effective immunopotentiating effect, in particular, when used in combination with an inactivated antigen. The oil adjuvant comprising a mineral oil as a principal component and represented by the Freund's adjuvant certainly shows a high immunopotentiating effect, but it suffers from various problems such that it causes a severe inoculation reaction and formation of aseptic festered lesions and granuloma in and around the inoculated sites and that there are externally observed edema, swelling, induration and necrosis and there is a suspicion that it has a tendency of remaining (remaining tendency) at the site of injection and accordingly, this becomes an obstacle to the application thereof to vaccines. If such local reactions remain in domestic animals, the meat thereof would not be fit for eating and therefore, such remaining tendency should desirably be reduced as low as possible. For this reason, the vaccines which make use of the oil adjuvant mainly comprising a mineral oil would sometimes be limited in the sites to be inoculated.

It is essential to enhance efficacy and duration of vaccine in order to ensure the prevention of a disease, or to achive an object of the vaccine. However, safety of the vaccine is much more important than efficacy and duration in the light of the fact that the vaccine is applied to human or veterinary use.

Under these circumstances, there have been conducted various studies to solve the foregoing problems. For instance, Japanese Examined Patent Publication (hereinafter referred to as "J.P. KOKOKU") No. Hei 6-81731 discloses a water-in-oil type oil-based adjuvant wherein an anhydrous mannitol/oleic acid ester as a surfactant and liquid paraffin is used as the oil component. WO91/00107 (TOKUHYO Hei 4-506521) discloses a low viscosity water-in-oil type oil-based adjuvant whose oil component used comprises a mixture of a metabolizable oil such as a vegetable oil and a non-metabolizable oil such as a mineral oil. Moreover, Japanese Un-Examined Patent Publication (hereinafter referred to as "J.P. KOKAI") No. Hei 6-172216 discloses an oil adjuvant vaccine which comprises a vegetable oil as the oil component and a mixture of a sorbitan fatty acid ester and a polyoxyethylene glycol sorbitan alkyl ester as a surfactant component, and J.P. KOKOKU No. Hei 6-39386 discloses an adjuvant live vaccine which is prepared by admixing a live immunogen with an oil-in-water type emulsion which comprises a mineral oil.

However, all of the foregoing oil adjuvant vaccines are insufficient not only in the local reaction observed after injection and the tendency of remaining at the site of injection, but also in the stability of the preparations as vaccines.

The vaccine should be effective and safe as high as possible since it is applied to human or veterinary use and it should be stable as high as possible while taking into consideration the fact that it is a pharmaceutical.

In case of oil adjuvant vaccines, however, it has been well-known that not only the immunopotentiating effect of these vaccines, but also the stability thereof as pharmaceutical preparations are considerably affected by, for instance, the types of emulsions and oil components used as well as the kinds of surfactants to be incorporated. In respect of, in particular, inactivated vaccines, it has been very difficult to prepare a vaccine which can show its effect of inducing sufficient protective immunity over a long period of time in good reproducibility.

In addition, there have also been proposed water-in-oil-in-water type oil adjuvant vaccines in order to eliminate the drawbacks of the conventional water-in-oil type oil adjuvant vaccines, i.e., the local reactions and the tendency of remaining at injected sites, but any conventional means has still suffered from problems of long term stability of the resulting pharmaceutical preparations and accordingly, the practical use of such vaccines would be far ahead.

SUMMARY OF THE INVENTION

The present invention relates to an oil adjuvant vaccine whose applications have conventionally been limited because of their undesirable local reactions, remaining-tendency and insufficient stability of pharmaceutical preparations and thus intends to solve the problems associated with the coventional such vaccines. Accordingly, an object of the present invention is to provide an oil adjuvant vaccine which can maintain a high antibody-producing ability over a long period of time without using any immunopotentiating substance in the formulation and which is not harmful to the living body and is excellent in the stability of the resulting pharmaceutical preparations.

The inventors of this invention have conducted various studies to accomplish the foregoing object. As a result, they have found out that a water-in-oil type oil adjuvant vaccine comprising (i) an oil component which is in a liquid state at ordinary temperature, (ii) an emulsifying agent which comprises a specific lipophilic non-ionic surfactant and a polyoxyethylene hydroxy fatty acid triglyceride and (iii) an aqueous phase containing a biologically acceptable and effective amount of an antigenic component; and a water-in-oil-in-water type oil adjuvant vaccine comprising an internal phase constituted by the above-mentioned water-in-oil type emulsion (i.e., the above-mentioned oil adjuvant) and an outer aqueous phase comprising a specific emulsifying agent exhibit excellent local safety upon being inoculated and also show an excellent ability to induce an antibody-production over a long period of time. Further, they have found out that an oil adjuvant vaccine which shows high stability even in a very low viscosity region and is excellent in the ability to induce an antibody-production and an ability of maintaining high antibody-productivity can be prepared by a method which comprises the steps of adding, to an oil component which is in a liquid state at ordinary temperature, a surfactant comprising a specific lipophilic non-ionic surfactant and a polyoxyethylene hydroxy fatty acid triglyceride, and a gel-like composite obtained by emulsifying a specific lipophilic non-ionic surfactant and an aqueous solution containing an amino acid or a salt thereof and a specific sugar or sugar alcohol; and then adding, to the resulting mixture, an aqueous phase containing antigens to thus form an emulsion. Further, they have found out that a water-in-oil-in-water type oil adjuvant vaccine which is excellent in safety and stability and can show excellent long-lasting ability to induce an antibody-production as compared with conventional vaccines of the same type by a method which comprises the steps of preparing a water-in-oil type oil adjuvant vaccine by the above-mentioned method, and then adding the water-in-oil type oil adjuvant vaccine to an aqueous phase containing a specific emulsifying agent to thus emulsify the same. Based on the above findings, they have completed the present invention.

According to a first aspect of the present invention, there is provided a water-in-oil type oil adjuvant vaccine comprising 20 to 90% by weight of an oil phase A) which is in a liquid state at ordinary temperature; 0.5 to 30% by weight of an emulsifying agent comprising a non-ionic surfactant B) which is a partial ester derived from a polyhydric alcohol carrying at least three hydroxyl groups and a fatty acid and which is in a liquid state at 40° C. and a polyoxyethylene (20 to 60 moles) hydroxy fatty acid triglyceride C); and 5 to 75% by weight of an aqueous phase D) containing a biologically acceptable and effective amount of antigens.

According to another aspect of the present invention, there is provided a water-in-oil-in-water type oil adjuvant vaccine comprising a water-in-oil type oil adjuvant phase comprising 30 to 90% by weight of an oil phase A) which is in a liquid state at ordinary temperature, 0.5 to 30% by weight of an emulsifying agent comprising a non-ionic surfactant B) which is a partial ester derived from a polyhydric alcohol carrying at least three hydroxyl groups and a fatty acid and which is in a liquid state at 40° C. and a polyoxyethylene (20 to 60 moles) hydroxy fatty acid triglyceride C) and 5 to 65% by weight of an aqueous phase D) containing a biologically acceptable and effective amount of antigens; and an outer aqueous phase F) comprising 0.2 to 20% by weight of an emulsifying agent which comprises a non-ionic surfactant and which ha s an overall HLB value of not less than 10.

EMBODIMENTS OF THE INVENTION

The component A) of the oil adjuvant vaccine according to the present invention is an oil component which is in a liquid state at ordinary temperature. The term "ordinary temperature" used herein means a temperature falling within the range of from 15° to 25° C.

The oil component which is in a liquid state at ordinary temperature and which can be used in the present invention may variously be selected from ester type oil bases or non-ester type oil bases which have commonly been used in, for instance, foods, drugs and cosmetics and which are in a liquid state at ordinary temperature. Examples of non-ester type oil bases which are in a liquid state at ordinary temperature include light liquid paraffins, squalene, squalane and polybutenes. In addition, examples of ester type oil bases which are in a liquid state at ordinary temperature include various esters derived from medium chain saturated fatty acids such as caprylic acid and capric acid or long chain unsaturated fatty acids such as oleic acid and linoleic acid, and alcohols; naturally occurring fatty acid esters, for instance, liquid vegetable oils such as peanut oil, olive oil, sunflower seed oil, safflower oil and jojoba oil and liquid oils originated from animals such as orange roughy oil, which may be used alone or in combination depending on the purposes. Oils such as ester derivatives of oleic acid and vegetable oils, among others, have various advantages such that they are relatively high stability to oxidation, they have high affinity to organ-tissues and their local stimulation and remaining-tendency can be reduced and therefore, it is preferred to use at least one member selected from only these metabolizable oils as the oil component. Moreover, it is particularly prefered to use an ester type oil base comprising an ester derived from a fatty acid, which comprises not less than 85% by weight of cis-Δ9-octadecenoic acid and not less than 90% by weight of cis-Δ9-alkenoic acids, and an alcohol such as glycerol, diglycerol, propylene glycol, ethyl alcohol, decyl alcohol and oleyl alcohol which comprises not less than 85% by weight of cis-Δ9-octadecenol and not less than 90% by weight of cis-Δ9-alkenols. Alternatively, it is also possible in the present invention to use a mixture of the foregoing ester type oil(s) with squalene.

The component B) used as one of the emulsifying agents which constitute the oil adjuvant vaccine of the present invention is a lipophilic non-ionic surfactant which is a partial ester derived from a polyhydric alcohol carrying at least three hydroxyl groups and a fatty acid and which is in a liquid state at 40° C. The foregoing partial ester varies depending on the kinds of the polyhydric alcohols used. For instance, if the polyhydric alcohol is glycerol carrying three hydroxyl groups, the partial ester is a mixture mainly comprising monoesters, diesters and a small amount of triesters thereof; if the polyhydric alcohol is diglycerol or sorbitan carrying 4 hydroxyl groups, the partial ester is a mixture mainly comprising monoesters, diesters and small amounts of triesters and tetraesters thereof. These partial esters may be used alone or in any combination inasmuch as they are in liquid states at a temperature of 40° C. and they are lipophilic.

Examples of such polyhydric alcohols carrying at least three hydroxyl groups, which are used as an ingredient for preparing the partial ester include glycerol, diglycerol, triglycerol, tetraglycerol, hexaglycerol, octaglycerol, decaglycerol, xylitol, sorbitol, mannitol and sorbitan.

Examples of fatty acids used for preparing the partial esters are a variety of known fatty acids such as caprylic acid, capric acid, lauric acid, oleic acid and linoleic acid, so far as they can react with the foregoing polyhydric alcohols to form the foregoing partial esters which are in liquid states at 40° C. Among these fatty acids, particularly preferred are the fatty acid comprising not less than 85% by weight of cis-Δ9-octadecenoic acid and not less than 90% by weight of cis-Δ9-alkenoic acids.

Particularly suitable partial esters used as the component B) are, for instance, glycerol monooleate, sorbitan monooleate, sorbitan dioleate, diglycerol monooleate and diglycerol dioleate, which are derived from the fatty acid comprising not less than 85% by weight of cis-Δ9-octadecenoic acid and not less than 90% by weight of cis-Δ9-alkenoic acids. Since these partial esters contain highly purified oleic acid which is incorporated therein as an acyl group, they are excellent in stability to oxidation which is required when used as emulsifying agents, can ensure a high degree of orientation between these surfactant molecules and accordingly, they are excellent in functional characteristics such as emulsion-stabilizing action. Therefore, these partial esters permit the improvement in the stability of the finally prepared oil adjuvant vaccines and substantial improvement in the safety when inoculated, as compared with conventional oleic acid derivatives which have presently been put on the market.

In the polyoxyethylene (20 to 60 moles) hydroxy fatty acid triglyceride used in the oil adjuvant vaccine of the present invention as the component C), examples of hydroxy fatty acid triglycerides are castor oil and hydrogenated castor oil. In this respect, if the average number of ethylene oxide is less than 20 moles, the use of such a component C) does not permit the formation of a stable emulsion in a low viscosity region and as a result, the use thereof never permits the preparation of a satisfactory oil adjuvant vaccine. On the other hand, if the average number of ethylene oxide exceeds 60 moles, the resulting emulsion has a tendency of easily causing the phase inversion of emulsion and thus the use thereof never permits the ultimate preparation of a satisfactory oil adjuvant vaccine. The amount of the polyoxyethylene hydroxy fatty acid triglyceride to be incorporated into the vaccine preferably ranges from about 0.5 to 10% by weight based on the total weight of the formulation (the total weight of the water-in-oil type oil adjuvant vaccine). If it is less than 0.5% by weight, the stability of the resulting emulsified vaccine may be reduced. On the other hand, if it exceeds 10% by weight, the resulting emulsion easily causes a phase inversion and the stability of the resulting vaccine may accordingly be reduced.

An amino acid or a salt thereof and a non-reducing sugar or a sugar alcohol having at least 5 hydroxyl groups in the molecule used in the present invention is hereinafter referred to as "component E)". The stability of the emulsified vaccine of the present invention can further be improved by incorporating, into the oil adjuvant vaccine, the component E), that is, an amino acid or a salt thereof and a non-reducing sugar or a sugar alcohol having at least 5 hydroxyl groups in the molecule. The amino acid or the salt thereof used herein may be selected from those commonly used in foods or pharmaceuticals specified in various standards such as "Japanese Pharmacopoeia", "Standards for Ingredients of Drugs not in the Japanese Pharmacopoeia" and "Japanese Pharmaceutical Excipients". Examples of amino acids are glycine, alanine, arginine hydrochloride, asparagine, aspartic acid, glutamine, glutamic acid, histidine, leucine, isoleucine, proline, hydroxyproline, serine, threonine, valine and phenylalanine, with neutral amino acids being preferred among them. Moreover, examples of amino acid salts are monovalent metal salts such as sodium and pottassium salts; and divalent metal salts such as calcium and magnesium salts. Among these amino acids and salts thereof, particularly preferred are sodium aspartate monohydrate, potassium aspartate dihydrate, sodium glutamate monohydrate and potassium glutamate monohydrate. These amino acids are in general in the L-forms, but isomers thereof such as D-form or the DL-forms which are mixture of these isomers may likewise be used in the present invention.

The foregoing non-reducing sugar or sugar alcohol having at least 5 hydroxyl groups in the molecule used herein may be selected from those commonly used in foods or pharmaceuticals specified in various standards such as "Japanese Pharmacopoeia", "Standards for Ingredients of Drugs not in the Japanese Pharmacopoeia" and "Japanese Pharmaceutical Excipients", with trehalose, xylitol, sorbitol, mannitol, lactitol being particularly preferably used in the invention.

The amounts of the amino acid or salt thereof and the non-reducing sugar or sugar alcohol having at least 5 hydroxyl groups in the molecule used herein suitably ranges from 0.01 to 10% by weight based on the total weight of the formulation (the total weight of the oil adjuvant vaccine), respectively.

In the oil adjuvant vaccine, the ratio of the oil component A) to the component D), i.e., the aqueous phase containing antigens may appropriately be selected depending on the applications, purposes of the adjuvant or the kind of the antigen selected. In particular, the oil adjuvant vaccine of the present invention maintains its high stability due to the use of a combination of a specific oil component and a specific emulsifying agent and correspondingly, the ratio of the oil component to the aqueous phase containing an antigen may vary over a wide range. In general, the ratio may suitably be selected so that the weight ratio of the oil component to the aqueous phase ranges from 90:5 to 20:75, preferably 80:15 to 30:65.

In the preparation of the adjuvant, the total amount of the foregoing component B), i.e., the non-ionic surfactant and the component C), i.e., the polyoxyethylene (20 to 60 moles) hydroxy fatty acid triglyceride desirably ranges from 0.5 to 30% by weight, preferably 3 to 20% by weight on the basis of the total weight of the formulation. This is because if it is less than 0.5% by weight, any stable emulsified system cannot be prepared, while the use of the emulsifying agent in an amount higher than 30% by weight results in the formation of an adjuvant exhibiting high reactivity at the injected local site and cannot provide any desired oil adjuvant vaccine of the present invention having high stability.

A first embodiment of the oil adjuvant vaccine according to the present invention relates to an oil adjuvant vaccine which comprises the foregoing oil component, emulsifying agent and aqueous phase containing an antigen and the oil adjuvant vaccine can, for instance, be prepared by the following method. The method comprises adding, to an oil component as the component A), a non-ionic surfactant [component B)] which is in a liquid state at 40° C. and a polyoxyethylene (20 to 60 moles) hydroxy fatty acid triglyceride [component C)], followed by mixing these ingredients with stirring, then adding an aqueous phase [component D)] containing a biologically acceptable and effective amount of antigens and mixing them with stirring to give an emulsion. This method permits the preparation of a water-in-oil type oil adjuvant vaccine which is in a good emulsified condition.

In the present invention, a water-in-oil type oil adjuvant vaccine which has a low viscosity and has high stability even when it is stored at a low temperature can be prepared, without impairing the safety thereof, by a method comprising the steps of adding, to an oil phase A) which is in a liquid state at ordinary temperature, a non-ionic surfactant B) which is a partial ester derived from a polyhydric alcohol carrying at least three hydroxyl groups and a fatty acid and which is in a liquid state at 40° C., a polyoxyethylene (20 to 60 moles) hydroxy fatty acid triglyceride C), and a product which is obtained by admixing the non-ionic surfactant as the component B) and an aqueous solution containing the component E), in a weight ratio: the non-ionic surfactant as the component B) to the aqueous solution of the component E) ranging from 1:1 to 1:20 and then emulsifying the mixture till a firm gel-like composite is formed; then admixing these ingredients to thus form a dispersion; adding an aqueous phase D) containing a biologically acceptable and effective amount of antigens to the resulting dispersion; and mixing them with stirring to thus emulsify the aqueous phase. If the temperature of the ingredients increases due to the action of a stirring machine in the foregoing step for preparing the firm gel-like composite comprising the component B), i.e., a non-ionic surfactant which is a partial ester derived from a polyhydric alcohol carrying at least three hydroxyl groups and a fatty acid and which is in a liquid state at 40° C. and the aqueous solution containing the component E), the stirring operatioin may be carried out while cooling the ingredients to maintain the temperature to a level of not more than ordinary temperature.

In this respect, the optimum mixing ratio of the component B) to the aqueous solution of the component E) can appropriately be selected depending on the kinds and concentrations of the amino acid or salt thereof and the non-reducing sugar or a sugar alcohol present in the aqueous solution of the component E). If the aqueous solution of the component E) is, for instance, an aqueous solution containing 5% by weight of sodium L-glutamate monohydrate and 5% by weight of lactitol, the weight ratio of the component B) to the aqueous solution of the component E) is suitably adjusted to the range of from 1:2 to 1:10. In addition, if the aqueous solution comprises 30% by weight of sodium L-glutamate monohydrate and 20% by weight of lactitol, the weight ratio of the component B) to the aqueous solution of the component E) is suitably adjusted to the range of from 1:2 to 1:15. In this regard, it is desirable that the concentration of the component E) in the aqueous solution be adjusted to a level as high as possible within the solubility range of the amino acid or salt thereof and the non-reducing sugar or sugar alcohol, respectively.

The second embodiment of the oil adjuvant vaccine according to the present invention relates to a water-in-oil-in-water type oil adjuvant vaccine which comprises an internal phase comprising the foregoing water-in-oil type oil adjuvant vaccine; and an outer aqueous phase comprising at least one non-ionic surfactant which has an overall HLB (hydrophile-lipophile balance) value of not less than 10.

In this specification, the "HLB"(hydrophile-lipophile balance) value is determined according to the equation proposed by W. C. Griffin (see W. C. Griffin, J. Soc. Cosmetic Chemists, 1949, 1, p. 311).

The emulsifying agent having an overall HLB value of not less than 10 and used in the outer phase which constitutes the water-in-oil-in-water type oil adjuvant vaccine of the present invention may be alone or any combination thereof provided that it has an overall HLB value of not less than 10. The non-ionic surfactant which has an overall HLB value of not less than 10 may be selected from those usually used in the field of pharmaceuticals, for instance, polyoxyethylene hydroxy fatty acid triglycerides, polyoxyethylene sorbitan fatty acid esters, polyoxyethylene alkyl(alkenyl) ethers, polyoxyethylene polyoxypropylene glycol, which have an overall HLB value of not less than 10.

Among these, polyoxyethylene hydroxy fatty acid triglycerides having an HLB of not less than 10 may be the same as those used as ingredients of the oil adjuvant vaccine, i.e., polyoxyethylene hydroxy fatty acid triglycerides such as castor oil and/or hydrogenated castor oil, which have an average number of ethylene oxide of not less than 20, preferably 20 to 60. This is because, the use of a polyoxyethylene hydroxy fatty acid triglycerides having an average number of ethylene oxide of less than 20 does not permit the stable dispersion of the water-in-oil type oil adjuvant serving as an internal phase into the outer phase and does not accordingly permit the formation of a good water-in-oil-in-water type oil adjuvant vaccine. On the other hand, if it exceeds 60, the resulting internal water-in-oil emulsion phase has a tendency of easily causing the phase inversion thereof and thus the use thereof never permits the ultimate preparation of a satisfactory water-in-oil-in-water type oil adjuvant vaccine.

Moreover, polyoxyethylene sorbitan fatty acid esters having an HLB value of not less than 10 may, for instance, be polyoxyethylene sorbitan unsaturated fatty acid (such as oleic acid) esters and polyoxyethylene sorbitan saturated fatty acid (such as lauric acid and caprylic acid) ester, which have an average ethylene oxide number of not less than 10. In particular, preferably used are polyoxyethylene sorbitan fatty acid esters in which the fatty acid comprises not less than 85% by weight of cis-Δ9-octadecenoic acid and not less than 90% by weight of cis-Δ9-alkenoic acids and which have an average number of ethylene oxide ranging from 10 to 40. This is because if the average ethylene oxide number is less than 10, the water-in-oil type oil adjuvant serving as the internal phase cannot stably be dispersed in the outer aqueous phase and accordingly the use thereof never permits the preparation of a satisfactory water-in-oil-in-water type oil adjuvant vaccine. On the other hand, if it exceeds 40, the water-in-oil type oil adjuvant serving as the internal phase has a tendency of easily causing the phase inversion of emulsion and thus the use thereof never permits the ultimate preparation of a satisfactory water-in-oil-in-water type oil adjuvant vaccine.

The polyoxyethylene alkyl(alkenyl) ethers may, for instance, be commonly known alkyl ether type surfactants such as polyoxyethylene alkyl ethers, for instance, polyoxyethylene lauryl ether and polyoxyethylene cetyl ether; and polyoxyethylene alkenyl ethers, for instance, polyoxyethylene oleyl ether. Preferred are those each carrying an alkyl (alkenyl) group having 12 to 18 carbon atoms and having an average ethylene oxide number of not less than 10 and preferably 10 to 40. In particular, polyoxyethylene oleyl ethers in which oleyl alcohols comprises not less than 85% by weight of cis-Δ9-octadecenol and not less than 90% by weight of cis-Δ9-alkenols and 10 to 40 moles of ethylene oxide. In this regard, if the number of carbon atoms in the alkyl (alkenyl) group is less than 12, the water-in-oil type oil adjuvant serving as the internal phase has a tendency of easily causing the phase inversion of emulsion and thus the use thereof never permits the preparation of a satisfactory water-in-oil-in-water type oil adjuvant vaccine, while if it exceeds 18, the water-in-oil type oil adjuvant serving as the internal phase cannot stably be dispersed in the outer aqueous phase and accordingly the use thereof never permits the ultimate preparation of a satisfactory water-in-oil-in-water type oil adjuvant vaccine. Moreover, the use of a polyoxyethylene alkyl(alkenyl) ether having an average number of ethylene oxide of less than 10 does not permit the stable dispersion of the water-in-oil type oil adjuvant serving as an internal phase into the outer phase and does not accordingly permit the formation of a good water-in-oil-in-water type oil adjuvant vaccine. On the other hand, if it exceeds 40, the water-in-oil type oil adjuvant serving as the internal phase has a tendency of easily causing the phase inversion of emulsion and thus the use thereof never permits the ultimate preparation of a satisfactory water-in-oil-in-water type oil adjuvant vaccine.

The polyoxyethylene polyoxypropylene glycol usable herein may be selected from those commonly used in pharmaceuticals and cosmetics which have an HLB value of not less than 10. Among these, preferred are those having an ethylene oxide number (average degree of polymerization) ranging from 50 to 200, a propylene oxide number (average degree of polymerization) ranging from 5 to 80 and the ratio of the molar number (average degree of polymerization) of ethylene oxide to that of propylene oxide of not less than 2:1. This is because if the molar ratio is less than 2:1, the water-in-oil type oil adjuvant serving as the internal phase cannot stably be dispersed in the outer aqueous phase and accordingly the use thereof would not permit the preparation of a satisfactory water-in-oil-in-water type oil adjuvant vaccine.

As explained earlier, the emulsifying agent used in the outer phase which constitutes the water-in-oil-in-water oil adjuvant vaccine of the present invention may be one having an HLB value of not less than 10 or a mixture of two or more emulsifying agents wherein at least one of the agents is non-ionic surfactant having a high HLB value and at least of the agents is non-ionic surfactant having a low HLB value and wherein the overall HLB value is not less than 10. In this respect, the non-ionic surfactants having a low HLB value usable herein may be selected from those commonly used in pharmaceutical field and so on such as sorbitan monooleate, sorbitan sesqui-oleate and glycerol monooleate. An example of the mixture of non-ionic surfactants having a high HLB value and non-ionic surfactants having a low HLB value includes those comprising polyoxyethylene sorbitan monooleate having an HLB value of 15.0 and sorbitan sesqui-oleate having an HLB value of 3.7. In this case, the former is mixed with the latter in a weight ratio of 2:1 to give a mixture of emulsifying agents having an overall HLB value of about 11.2.

In the present invention, the stability of the intended water-in-oil-in-water type oil adjuvant vaccine can further be improved if using, as the emulsifying agent incorporated into the outer phase, a combination of the foregoing mixture of emulsifying agents which has an overall HLB value of not less than 10 with a glycerophospholipid.

The glycerophospholipids used in combination with the mixture of emulsifying agents which has an overall HLB value of not less than 10 usable herein may variously be selected from naturally occurring glycerophospholipids such as those derived from soybean (e.g., soybean lecithin and hydrogenated soybean lecithin), those derived from egg yolk (e.g., egg yolk phospholipid and hydrogenated egg yolk phospholipid); various highly purified phospholipids (e.g., phosphatidylcholine and phosphatidylethanolamine); and lysophospholipids, which may be used alone or in any combination. When using a combination of the foregoing mixture of emulsifying agents which has an overall HLB value of not less than 10 and a glycerophospholipid, the mixing ratio (by weight): non-ionic surfactant mixture/ glycerophospholipid is suitably adjusted to the range of from 20:1 to 1:2.

The amount of the emulsifying agent used in the outer phase which constitutes the water-in-oil-in-water type oil adjuvant vaccine of the present invention ranges from 0.2 to 20% by weight and particularly preferably 0.5 to 10% by weight on the basis of the total weight of the outer phase. This is because, if the amount of the emulsifying agent is less than 0.2% by weight, any stable water-in-oil-in-water type emulsion cannot be obtained, while if it exceeds 20% by weight, the viscosity of the resulting oil adjuvant vaccine increases to such a level that the vaccine would not be good for inoculation and the safety thereof in the case of injection, the safety thereof is sometimes lowered.

In addition, the mixing ratio of the water-in-oil type oil adjuvant phase serving as the internal phase to the outer aqueous phase in the water-in-oil-in-water type oil adjuvant vaccine according to the present invention may suitably be adjusted, depending on the purposes, so that it falls within the range of from 2:1 to 1:10 as expressed in terms of the weight ratio.

In the water-in-oil-in-water type oil adjuvant vaccine thus prepared, antigens can efficiently be incorporated into the internal aqueous phase by the following two-stage method in which a water-in-oil type oil adjuvant vaccine is prepared, in advance, using an aqueous phase containing the antigen and then adding the resulting water-in-oil emulsion as an internal phase to an outer aqueous phase comprising a specific emulsifying agent to thus form an emulsion.

The water-in-oil-in-water type oil adjuvant vaccine according to the present invention may, for instance, be prepared by the following method. The method comprises the steps of preparing, in advance, an antigen-containing water-in-oil type oil adjuvant vaccine according to the present invention, and then adding the water-in-oil type oil adjuvant vaccine to an aqueous phase which comprises a mixed emulsifying agent containing at least one non-ionic surfactant and having an overall HLB value of not less than 10 or a combination of a mixed emulsifying agent containing at least one non-ionic surfactant and having an overall HLB value of not less than 10 with a glycerophospholipid to thus again emulsify the antigen-containing water-in-oil type oil adjuvant vaccine. In the present invention, the two-stage emulsifying method permits the formation of a highly stable water-in-oil-in-water type oil adjuvant vaccine which is excellent in safety.

More specifically, a water-in-oil-in-water type oil adjuvant vaccine having more higher stability can be prepared, without impairing the safety thereof, by first adding, to an oil component which is in a liquid state at ordinary temperature, a lipophilic non-ionic surfactant (component B) which is a partial ester derived from a polyhydric alcohol carrying at least three hydroxyl groups and a fatty acid and in a liquid state at 40° C., a polyoxyethylene (20 to 60 moles) hydroxy fatty acid triglyceride (component C) and a product obtained by mixing the non-ionic surfactant as the component B and an aqueous solution containing a component E in a weight ratio: the former to the latter ranging from 1:1 to 1:20 and then stirring these ingredients till a firm gel-like composite is formed; then mixing and dispersing them; thereafter adding an outer aqueous phase (component D) containing a biologically acceptable and effective amount of antigens to the resulting dispersion, then mixing with stirring to emulsify the aqueous phase into the oil phase and to thus give a highly stable water-in-oil type oil adjuvant vaccine; and then adding the water-in-oil type oil adjuvant vaccine to an outer aqueous phase which comprises a mixed emulsifying agent containing at least one non-ionic surfactant and having an overall HLB value of not less than 10 or a combination of a mixed emulsifying agent containing at least one non-ionic surfactant and having an overall HLB value of not less than 10 with a glycerophospholipid to thus re-emulsify the antigen-containing water-in-oil type oil adjuvant vaccine into the aqueous phase.

The aqueous phase of the water-in-oil type oil adjuvant vaccine of the present invention, the internal aqueous phase of the water-in-oil-in-water type oil adjuvant vaccine of the present invention, or the outer aqueous phase of the water-in-oil-in-water type oil adjuvant vaccine of the present invention, may be selected from those used in conventional vaccines such as phosphate buffer solutions, physiological salt solution or phosphate buffered saline.

In the water-in-oil-in-water type oil adjuvant vaccine of the present invention, the antigen may be present, depending on, for instance, the conditions for the preparation, only in the internal aqueous phase within the water-in-oil type emulsion serving as the internal phase, or in the both aqueous phases, i.e., the internal aqueous phase and the outer aqueous phase due to partial leakage thereof from the internal aqueous phase, but in any case, the effect of the oil adjuvant vaccine of the present invention would not be impaired at all.

In the present invention, the oil phase and the internal aqueous phase constituting the oil adjuvant vaccine, the outer aqueous phase constituting the water-in-oil-in-water type oil adjuvant vaccine or the like may of course comprise various components which are not directly involved in the adjuvant activity such as a buffer, a stabilizer and/or an osmotic pressure-regulating component, which are used in various pharmaceuticals.

Moreover, there may be used any means which generally permits emulsification, for instance, emulsifiers currently used such as a homomixer, a homogenizer and CLEARMIX (available from M TECHNIQUE Co., Ltd.) and a membrane-emulsifier which makes use of a porous glass membrane, when preparing the oil adjuvant vaccine of the present invention.

Antigens to be incorporated into the aqueous phase constituting the oil adjuvant vaccine according to the present invention may include various kinds and various forms of antigens, for instance, killed bacterial cells and inactivated virus particles commonly used in the preparation of vaccines as well as protective antigens such as attachment proteins and envelopes. However, wide variety of intended antigens may be used in a biologically acceptable and effective amount since the oil adjuvant vaccine of the present invention which is very stable can easily be obtained by the use of a combination of a specific oil component and a specific emulsifying agent.

Furthermore, the oil adjuvant vaccine of the present invention may of course comprise, in the emulsion, various drugs such as antibiotics in place of the antigen.

As has been discussed above in detail, the present invention permits the injectable preparation of various kinds of pharmaceutical compositions such as oil adjuvant vaccines by variously selecting components to be incorporated into the compositions. For instance, vaccines for veterinary use may induce immunopotentiation by administrating the same through subcutaneous injection or intramuscular injection and by administration thereof through oral, rectal and nasal routes, but the routes of administration may appropriately be selected depending on each particular purpose.

When preparing the adjuvant, constituents such as the oil base, surfactants and aqueous phase to be used must be sterilized. The sterilization method may be selected while taking into consideration the characteristic properties of these compounds.

As has been explained above, the oil adjuvant vaccine prepared by the present invention is in a quite stable and high quality emulsion. Therefore, the vaccine is excellent in stability and safety and can be administered to a variety of organisms while ensuring both efficacy and safety.

The present invention will hereinafter be described in more detail with reference to the following Examples, but the present invention is not limited to these specific Examples. In the following Examples, the term "part" means "part by weight" unless otherwise specified.

EXAMPLES
[Preparation of Oil Adjuvant Vaccine]

The oil adjuvant vaccines used in the following Examples each was prepared by the following method. All of the components included in the formulations were sterilized by heating or filtration which was selected while taking into consideration the characteristic properties of each particular component. Moreover, all operations such as stirring and emulsification were performed within a clean bench under sterilization conditions.

Example 1

Vaccine a

In this Example, ethyl oleate ["NOFABLE EO-90", available from NOF CORPORATION; acyl composition: cis-$\Delta$9-octadecenoic acid content of 88% by weight and cis-$\Delta$9-alkenoic acids content of 94% by weight] was used as the component A. To 12 parts of the oil component, there were added 1.6 part of sorbitan sesqui-oleate ["NOFABLE SO-992", available from NOF CORPORATION; acyl composition: cis-$\Delta$9-octadecenoic acid content of 99% by weight and cis-$\Delta$9-alkenoic acids content of 99% by weight] and 0.4 part of polyoxyethylene(40) hydrogenated castor oil heated to 50° C., followed by sufficient stirring, gradual addition of 6 parts of an aqueous phase (phosphate buffered saline) containing an antigen to the foregoing mixture with stirring and then mixing and emulsifying at ordinary temperature and 8000 rpm for 10 minutes using CLEARMIX CLM-0.8S (available from M TECHNIQUE Co., Ltd.) to thus give a water-in-oil type oil adjuvant vaccine a.

Example 2

Vaccine b

In this Example, the component A comprised a mixture of 6 parts of purified sunflower seed oil and 6 parts of squalene. To the oil component, there were added 1.6 part of sorbitan sesqui-oleate ["NOFABLE SO-902", available from NOF CORPORATION; acyl composition: cis-$\Delta$9-octadecenoic acid content of 88% by weight and cis-$\Delta$9-alkenoic acids content of 94% by weight] and 0.4 part of polyoxyethylene (40) hydrogenated castor oil heated to 50° C., followed by sufficient stirring, gradual addition of 8 parts of an aqueous phase (phosphate buffered saline) containing an antigen to the foregoing mixture with stirring and then mixing and emulsifying the resulting mixture by the same procedures used in Example 1 to thus give a water-in-oil type oil adjuvant vaccine b.

Example 3

Vaccine c

In this Example, oleyl oleate ["NOFABLE OO-9080", available from NOF CORPORATION; acyl composition: cis-$\Delta$9-octadecenoic acid content of 88% by weight and cis-$\Delta$9-alkenoic acids content of 94% by weight] was used as the component A. To 12 parts of the oil component, there were added 0.8 part of sorbitan sesqui-oleate ["NOFABLE SO-902", available from NOF CORPORATION; acyl composition: cis-$\Delta$9-octadecenoic acid content of 88% by weight and cis-$\Delta$9-alkenoic acids content of 94% by weight], 0.7 part of glycerol monooleate ["NOFABLE GO-901", available from NOF CORPORATION; acyl composition: cis-$\Delta$9-octadecenoic acid content of 88% by weight and cis-$\Delta$9-alkenoic acids content of 94% by weight] and 0.5 part of polyoxyethylene(40) hydrogenated castor oil heated to 50° C., followed by sufficient stirring, gradually adding 8 parts of an aqueous phase (phosphate buffered saline) containing an antigen to the foregoing mixture with stirring and then mixing and emulsifying the resulting mixture by the same procedures used in Example 1 to thus give a water-in-oil type oil adjuvant vaccine c.

Example 4

Vaccine X1

In this Example, there were used 5 parts of glycerol monooleate ["NOFABLE GO-901", available from NOF CORPORATION; acyl composition: cis-$\Delta$9-octadecenoic acid content of 88% by weight and cis-$\Delta$9-alkenoic acids content of 94% by weight] as the component B and an aqueous solution obtained by dissolving 3 parts of sodium L-glutamate monohydrate and one part of mannitol in 6 parts of distilled water as the component E. The component B and the aqueous solution of the component E were mixed and emulsified at ordinary temperature and 10,000 rpm for 10 minutes in CLEARMIX CLM-0.8S (available from M TECHNIQUE Co., Ltd.) to give a gel-like product.

Then, to a mixture of 6 parts of oleyl oleate ["NOFABLE OO-9080", available from NOF CORPORATION; acyl composition: cis-Δ9-octadecenoic acid content of 88% by weight and cis-Δ9-alkenoic acids content of 94% by weight] and 6 parts of squalene as the component A, there were added 1.6 part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight] as the component B and 0.4 part of polyoxyethylene(40) hydrogenated castor oil heated to 50° C. as the component C, followed by sufficient stirring, addition of one part of the foregoing gel-like product to the resulting mixture to thus disperse the former in the oil phase, gradual addition of 8 parts of an aqueous phase comprising phosphate buffered saline containing an antigen to the foregoing mixture with stirring and then mixing and emulsifying at ordinary temperature and 8000 rpm for 10 minutes using CLEARMIX CLM-0.8S (available from M TECHNIQUE Co., Ltd.) to thus give a water-in-oil type oil adjuvant vaccine X1.

Example 5

Vaccine X2

In this Example, there were used 6 parts of diglycerol monooleate ["NOFABLE PGO-9021L", available from NOF CORPORATION; acyl composition: cis-Δ9-octadecenoicacid content of 88% by weight and cis-Δ9-alkenoic acids content of 94% by weight] as the component B and an aqueous solution obtained by dissolving 4 parts of sodium L-glutamate monohydrate and one part of lactitol in 7 parts of distilled water as the component E. The component B and the aqueous solution of the component E were mixted and emulsified by the same procedures used in Example 4 to give a gel-like product.

Then, to a mixture of 6 parts of purified sunflower seed oil and 6 parts of ethyl oleate ["NOFABLE EO-90", available from NOF CORPORATION; acyl composition: cis-Δ9-octadecenoic acid content of 88% by weight and cis-Δ9-alkenoic acids content of 94% by weight] as the oil component, there were added 1.6 part of sorbitan sesqui-oleate ["NONION OP-83RAT", available from NOF CORPORATION; acyl composition: cis-Δ9-octadecenoic acid content of 55% by weight and cis-Δ9-alkenoic acids content of 78% by weight] and 0.4 part of polyoxyethylene(40) hydrogenated castor oil heated to 50 ° C., followed by sufficient stirring, addition of one part of the foregoing gel-like product to the resulting mixture to thus disperse the former in the oil phase, gradual addition of 8 parts of an aqueous phase comprising phosphate buffered saline containing an antigen to the foregoing mixture with stirring and then mixing and emulsifying by the same procedures used in Example 4 to thus give a water-in-oil type oil adjuvant vaccine X2.

Example 6

Vaccine X3

In this Example, there were used 4 parts of glycerol monooleate ["NOFABLE GO-991P", available from NOF CORPORATION; acyl composition: cis-Δ9-octadecenoicacid content of 99% by weight and cis-Δ9-alkenoic acids content of 99% by weight] and 4 parts of glycerol dioleate ["NOFABLE GO-902P", available from NOF CORPORATION; acyl composition: cis-Δ9-octadecenoicacid content of 88% by weight and cis-Δ9-alkenoic acids content of 94% by weight] as the component B and an aqueous solution obtained by dissolving 4 parts of sodium L-aspartate monohydrate and one part of trehalose in 11 parts of distilled water as the component E. The component B and the component E were mixed and emulsified by the same procedures used in Example 4 to give a gel-like product.

Then, to a mixture of 8 parts of decyl oleate ["NOFABLE DO-99", available from NOF CORPORATION; acyl composition: cis-Δ9-octadecenoic acid content of 99% by weight and cis-Δ9-alkenoic acids content of 99% by weight] and 4 parts of squalene as the oil component, there were added 0.8 part of sorbitan sesqui-oleate ["NOFABLE SO-992", available from NOF CORPORATION; acyl composition: cis-Δ9-octadecenoicacid content of 99% by weight and cis-Δ9-alkenoic acids content of 99% by weight], 1.2 part of glycerol monooleate ["NOFABLE GO-991", available from NOF CORPORATION; acyl composition: cis-Δ9-octadecenoic acid content of 99% by weight and cis-Δ9-alkenoic acids content of 99% by weight] and 0.4 part of polyoxyethylene(40) hydrogenated castor oil heated to 50° C., followed by sufficient stirring, addition of one part of the foregoing gel-like product to the resulting mixture to thus disperse the former in the oil phase, gradual addition of 10 parts of an aqueous phase comprising phosphate buffered saline containing an antigen to the foregoing mixture with stirring and then mixing and emulsifying by the same procedures used in Example 4 to thus give a water-in-oil type oil adjuvant vaccine X3.

Example 7

Vaccine d

In this Example, ethyl oleate ["NOFABLE EO-99", available from NOF CORPORATION; acyl composition: cis-Δ9-octadecenoic acid content of 99% by weight and cis-Δ9-alkenoic acids content of 99% by weight] was used as the component A. To 12 parts of the oil component, there were added 1.7 part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight] and 0.3 part of polyoxyethylene(40) hydrogenated castor oil heated to 50 ° C., followed by sufficient stirring, gradual addition of 8 parts of an aqueous phase (phosphate buffered saline) containing an antigen to the foregoing mixture with stirring and then mixing and emulsifying by the same procedures used in Example 1 to thus give a water-in-oil type oil adjuvant vaccine.

Then 0.4 part of polyoxyethylene(160) polyoxypropylene (30) glycol (having an HLB value of 16.0) as a surfactant was added to and uniformly dissolved in 10 parts of phosphate buffered saline, followed by gradual addition of 10 parts of the foregoing water-in-oil type oil adjuvant to the dispersion with stirring and then mixing and emulsifying at ordinary temperature and 8,000 rpm for 5 minutes using CLEARMIX CLM-0.8S (available from M TECHNIQUE Co., Ltd.) to thus give a water-in-oil-in-water type oil adjuvant vaccine d.

Example 8

Vaccine e

In this Example, a mixture of 6 parts of purified jojoba oil and 6 parts of squalene was used as the component A. To the oil component, there were added 1.6 part of sorbitan sesquioleate ["NONION OP-83RAT", available from NOF CORPORATION; acyl composition: cis-Δ9-octadecenoic acid content of 55% by weight and cis-Δ9-alkenoic acids content of 78% by weight] and 0.4 part of polyoxyethylene (40) hydrogenated castor oil heated to 50 ° C., followed by sufficient stirring, gradual addition of 8 parts of an aqueous phase (phosphate buffered saline) containing an antigen to the foregoing mixture with stirring and then mixing and emulsifying by the same procedures used in Example 1 to thus give a water-in-oil type oil adjuvant vaccine.

Then 0.2 part of polyoxyethylene(20) sorbitan monooleate ("NONION OT-221" available from NOF CORPORATION; acyl composition: cis-Δ9-octadecenoicacid content of 55% by weight and cis-Δ9-alkenoic acids content of 78% by weight; HLB: 15.8) as a surfactant was added to and uniformly dissolved in 10 parts of phosphate buffered saline, followed by gradual addition of 10 parts of the foregoing water-in-oil type oil adjuvant to the dispersion with stirring and then mixing and emulsifying by the same method used in Example 7 to thus give a water-in-oil-in-water type oil adjuvant vaccine e.

Example 9
Vaccine f

In this Example, there was used, as the component A, a mixture comprising 6 parts of oleyl oleate ["NOFABLE OO-9080", available from NOF CORPORATION; acyl composition: cis-Δ9-octadecenoic acid content of 88% by weight and cis-Δ9-alkenoic acids content of 94% by weight] and 6 parts of glycerol trioleate ["NOFABLE GO-993", available from NOF CORPORATION; acyl composition: cis-Δ9-octadecenoicacid content of 99% by weight and cis-Δ9-alkenoic acids content of 99% by weight]. To the oil component, there were added 0.9 part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight], 0.8 part of glycerol monooleate ["NOFABLE GO-991", available from NOF CORPORATION; acyl composition: cis-Δ9-octadecenoic acid content of 99% by weight and cis-Δ9-alkenoic acids content of 99% by weight] and 0.3 part of polyoxyethylene(40) hydrogenated castor oil heated to 50° C., followed by sufficient stirring, gradual addition of 8 parts of an aqueous phase (phosphate buffered saline) containing an antigen to the foregoing mixture with stirring and then mixing and emulsifying by the same procedures used in Example 1 to thus give a water-in-oil type oil adjuvant vaccine.

Then 0.14 part of polyoxyethylene(60) hydrogenated castor oil (having an HLB value of 14.8) and 0.06 part of hydrogenated soybean lecithin ("COATSOME NC-21" available from NOF CORPORATION) as surfactants were added to and uniformly dissloved in 10 parts of phosphate buffered saline, followed by gradual addition of 10 parts of the foregoing water-in-oil type oil adjuvant to the dispersion with stirring and then mixing and emulsifying by the same method used in Example 7 to thus give a water-in-oil-in-water type oil adjuvant vaccine f.

Example 10
Vaccine X4

In this Example, there were used 5 parts of glycerol monooleate ["NOFABLE GO-901", available from NOF CORPORATION; acyl composition: cis-Δ9-octadecenoic acid content of 88% by weight and cis-Δ9-alkenoic acids content of 94% by weight] as the component B and an aqueous solution obtained by dissolving 3 parts of sodium L-glutamate monohydrate and one part of mannitol in 6 parts of distilled water as the component E. The component B and the component E were mixed and emulsified by the same procedures used in Example 4 to give a gel-like product.

Then, to 12 parts of ethyl oleate ["NOFABLE EO-90", available from NOF CORPORATION; acyl composition: cis-Δ9-octadecenoic acid content of 88% by weight and cis-Δ9-alkenoic acids content of 94% by weight] as the oil component, there were added 1.7 part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight] and 0.3 part of polyoxyethylene(40) hydrogenated castor oil heated to 50° C., followed by sufficient stirring, addition of one part of the foregoing gel-like product to the resulting mixture to thus disperse the former in the oil phase, gradual addition of 8 parts of an aqueous phase comprising phosphate buffered saline containing an antigen to therforegoing mixture with stirring and then mixing and emulsifying by the same procedures used in Example 4 to thus give a water-in-oil type oil adjuvant vaccine.

Then 0.4 part of polyoxyethylene(160) polyoxypropylene (30) glycol (having an HLB value of 16.0) as a surfactant was added to and uniformly dissolved in 10 parts of phosphate buffered saline, followed by gradual addition of 10 parts of the foregoing water-in-oil type oil adjuvant vaccine to the dispersion with stirring and then mixing and emulsifying and mixing at ordinary temperature and 8,000 rpm for 5 minutes using CLEARMIX CLM-0.8S (available from M TECHNIQUE Co., Ltd.) to thus give a water-in-oil-in-water type oil adjuvant vaccine X4.

Example 11
Vaccine X5

In this Example, there were used 6 parts of sorbitan monooleate ["NOFABLE SO-901", available from NOF CORPORATION; acyl composition: cis-Δ9-octadecenoic acid content of 88% by weight and cis-Δ9-alkenoic acids content of 94% by weight] as the component B and an aqueous solution obtained by dissolving 4 parts of sodium L-glutamate monohydrate and one part of lactitol in 7 parts of distilled water as the component E. The component B and the component E were mixed and emulsified by the same procedures used in Example 4 to give a gel-like product.

Then, to a mixture comprising 10 parts of purified sunflower seed oil and 2 parts of squalane as the oil component, there were added 1.7 part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight] and 0.3 part of polyoxyethylene(40) hydrogenated castor oil heated to 50° C., followed by sufficient stirring, addition of one part of the foregoing gel-like product to the resulting mixture to thus disperse the former in the oil phase, gradual addition of 8 parts of an aqueous phase comprising phosphate buffered saline containing an antigen to the foregoing mixture with stirring and then mixing and emulsifying by the same procedures used in Example 1 to thus give a water-in-oil type oil adjuvant vaccine.

Then 0.14 part of polyoxyethylene(20) sorbitan monooleate ("NONION OT-221" available from NOF CORPORATION; acyl composition: cis-Δ9-octadecenoic acid content of 55% by weight and cis-Δ9-alkenoic acids content of 78% by weight; HLB: 15.8) and 0.06 part of hydrogenated soybean lecithin ("COATSOME NC-21" available from NOF CORPORATION) as surfactants were added to and uniformly dispersed in 10 parts of phosphate buffered saline, followed by gradual addition of 10 parts of the foregoing water-in-oil type oil adjuvant vaccine to the dispersion with stirring and then mixing and emulsifying by the same method used in Example 7 to thus give a water-in-oil-in-water type oil adjuvant vaccine X5.

Comparative Example 1
Vaccine g

To 6 parts of light liquid paraffin ("CRYSTOL 52" available from ESSO Corporation) as the oil component, there were added 0.8 part of sorbitan sesqui-oleate ("NONION OP-83RAT", available from NOF CORPORATION; acyl composition: cis-Δ9-octadecenoic acid content of 55% by weight and cis-Δ9-alkenoic acids content of 83% by weight) and 0.2 part of polyoxyethylene(20) sorbitan monooleate ("NONION OT-221", available from NOF CORPORATION; acyl composition: cis-Δ9-octadecenoic acid content of 55% by weight and cis-Δ9-alkenoic acids content of 78% by weight), followed by gradual addition of 3 parts of an aqueous phase (phosphate buffered saline) containing an antigen with sufficient stirring and then mixing and emulsifying by the same method used in Example 1 to give a comparative water-in-oil type oil adjuvant vaccine g.

Comparative Example 2

Vaccine h

To a mixture comprising 6 parts of oleyl oleate ("NOFABLE OO-9080", available from NOF CORPORATION; acyl composition: cis-Δ9-octadecenoic acid content of 88% by weight and cis-Δ9-alkenoic acids content of 94% by weight) and 6 parts of squalane as the component A, there were added 1.6 part of sorbitan sesqui-oleate ("NONION OP-83RAT", available from NOF CORPORATION; acyl composition: cis-Δ9-octadecenoic acid content of 55% by weight and cis-Δ9-alkenoic acids content of 78% by weight) and 0.4 pmonooleate (xyethylene(20) sorbitan monooleate ("NONION OT-221", available from NOF CORPORATION; acyl composition: cis-Δ9-octadecenoicacid content of 55% by weight and cis-Δ9-alkenoic acids content of 78% by weight), followed by sufficient stirring, gradual addition of 8 parts of an aqueous phase (phosphate buffered saline) containing an antigen with stirring and then mixing and emulsifying by the same method used in Example 1 to give a comparative water-in-oil type oil adjuvant vaccine h.

Comparative Example 3

Vaccine i

To a mixture comprising 6 parts of oleyl oleate ("NOFABLE OO-9080", available from NOF CORPORATION; acyl composition: cis-Δ9-octadecenoic acid content of 88% by weight and cis-Δ9-alkenoic acids content of 94% by weight) and 6 parts of squalane as the component A, there were added 1.6 part of sorbitan sesqui-oleate ("NONION OP-83RAT", available from NOF CORPORATION; acyl composition: cis-Δ9-octadecenoic acid content of 55% by weight and cis-Δ9-alkenoic acids content of 78% by weight) and 0.4 part of polyoxyethylene(20) sorbitan monooleate ("NONION OT-221", available from NOF CORPORATION; acyl composition: cis-Δ9-octadecenoicacid content of 55% by weight and cis-Δ9-alkenoic acids content of 78% by weight), followed by sufficient stirring, gradual addition of 8 parts of an aqueous phase (phosphate buffered saline) containing an antigen with stirring and then mixing and emulsifying by the same method used in Example 1 to give a water-in-oil type oil adjuvant vaccine.

Then 0.14 part of polyoxyethylene(60) hydrogenated castor oil (HLB: 14.8) and 0.06 part of hydrogenated soybean lecithin ("COATSOME NC-21" available from NOF CORPORATION) as surfactants were added to and uniformly dispersed in 10 parts of phosphate buffered saline, followed by gradual addition of 10 parts of the foregoing water-in-oil type oil adjuvant to the dispersion with stirring and then mixing and emulsifying by the same method used in Example 7 to thus give a comparative water-in-oil-in-water type oil adjuvant vaccine i.

Comparative Example 4

Vaccine Y1

A gel-like product was prepared by emulsifying 5 parts of sorbitan monooleate ["NOFABLE SO-901", available from NOF CORPORATION; acyl composition: cis-Δ9-octadecenoic acid content of 88% by weight and cis-Δ9-alkenoic acids content of 94% by weight] and an aqueous solution obtained by dissolving 4 parts of lactitol in 6 parts of distilled water by the same method used in Example 4.

Then, to 12 parts of glycerol trioleate ["NOFABLE GO-903", available from NOF CORPORATION; acyl composition: cis-Δ9-octadecenoic acid content of 88% by weight and cis-Δ9-alkenoic acids content of 94% by weight], there were added one part of sorbitan sesqui-oleate ["NOFABLE SO-902", available from NOF CORPORATION; acyl composition: cis-Δ9-octadecenoic acid content of 88% by weight and cis-Δ9-alkenoic acids content of 94% by weight] and 0.5 part of polyoxyethylene(20) sorbitan monooleate ("NONION OT-221", available from NOF CORPORATION; acyl composition: cis-Δ9-octadecenoic acid content of 55% by weight and cis-Δ9-alkenoic acids content of 78% by weight), followed by sufficient stirring, addition of one part of the foregoing gel-like product to the resulting mixture to thus disperse the former in the oil phase, gradual addition of 6 parts of an aqueous phase comprising phosphate buffered saline containing an antigen to the foregoing mixture with stirring and then mixing and emulsifying by the same procedures used in Example 4 to thus give a comparative water-in-oil type oil adjuvant vaccine Y1.

Comparative Example 5

Vaccine Y2

To 6 parts of light liquid paraffin ("CRYSTOL 52" available from ESSO Corporation) as the oil component, there were added 0.8 part of sorbitan sesqui-oleate ("NONION OP-83RAT", available from NOF CORPORATION; acyl composition: cis-Δ9-octadecenoic acid content of 55% by weight and cis-Δ9-alkenoic acids content of 78% by weight) and 0.2 part of polyoxyethylene(20) sorbitan monooleate ("NONION OT-221", available from NOF CORPORATION; acyl composition: cis-Δ9-octadecenoic acid content of 55% by weight and cis-Δ9-alkenoic acids content of 78% by weight), followed by gradual addition of 3 parts of an aqueous phase comprising phosphate buffered saline containing an antigen with sufficient stirring, and then mixing and emulsifying by the same method used in Example 1 to give a water-in-oil type oil adjuvant vaccine.

Then 0.2 part of polyoxyethylene(60) hydrogenated castor oil (HLB: 14.8) as a surfactant was added to and uniformly dispersed in 10 parts of phosphate buffered saline, followed by gradual addition of 10 parts of the foregoing water-in-oil type oil adjuvant vaccine to the dispersion with stirring and then mixing and emulsifying by the same method used in Example 10 to thus give a comparative water-in-oil-in-water type oil adjuvant vaccine Y2.

Immunization Tests

Then immunization tests were carried out using specific oil adjuvant vaccines containing various antigens. In the identification of individual vaccines, each symbol attached to a specific vaccine indicates that the corresponding vaccine is one prepared on the basis of the formulation disclosed in Example or Comparative Example and specified by each corresponding symbol.

Test Example 1

Inactivated Vaccine for Swine Actinobacillus Infectious Disease

Actinobacillus pleuropneumoniae NG-22 strain (serotype 2) was inoculated into a medium, followed by aeration-spinner culture at 37° C., inactivation of the resulting culture medium with formalin, collection of the bacterial cells through centrifugation and washing of the cells. The resulting cells were used as an antigen. The antigen was dispersed in phosphate buffered saline in a concentration of $10^{10}$ CFU (Colony Forming Unit) (prior to inactivation) per dose and the resulting dispersion was used as an antigen-containing aqueous phase.

With regard to immunized groups (each group comprised five 4-week-old SPF (specific pathogen free) swines), 1 ml/swine of the vaccine a, c or X2 or 2 ml/swine of the vaccine d, f or X4 was intramuscularly injected two times at intervals of 4 weeks. While 1 ml/swine of the vaccine g or h or 2 ml/swine of the vaccine i or Y2 was intramuscularly injected, two times, to each swine belonging to comparative immunized groups (each group comprised five 4-week-old SPF swines) at intervals of 4 weeks. Moreover, non-immunized control group comprised five swines and the control group was domiciled with either of the immunized groups. Each animal was inspected for the clinical symptoms including the observation of the site of injection for 2 weeks after each vaccination, the serum of each animal was collected at proper intervals throughout the test period and the sera were inspected for the antibody titer as determined by the complement-fixation (CF) test. The site of injection was examined by autopsy after 16 weeks from the initial injection of the vaccine to thus determine the size and distribution of nodules formed which were evaluated on the basis of the lesion score (none: 0; ~severe: 3), followed by calculation of the average of 5 animals in each group.

The results of safety are listed in Table 1. The immunized groups did not become feverish and did not show any abnormality in the clinical symptoms. In the comparative immunized groups, there were observed transitory increase in the body temperature and became depressed. In the autopsy after 16 weeks from the initial vaccine-injection, any particular lesion was not observed for the immunized groups, but there were observed nodules which would be formed due to the injected substances for the comparative immunized groups.

TABLE 1

Safety of Inactivated Vaccine for Swine Actinobacillus Infectious Disease

| Test Group | Vaccine | After Initial Immunization C.S.[1] | B.T.[2] | After Booster C.S.[1] | B.T.[2] | Lesion Score |
|---|---|---|---|---|---|---|
| Immunized Groups | Vaccine a | 0/5[3] | 0/5[3] | 0/5 | 0/5 | 0 |
| | Vaccine c | 0/5 | 0/5 | 0/5 | 0/5 | 0 |
| | Vaccine d | 0/5 | 0/5 | 0/5 | 0/5 | 0 |
| | Vaccine f | 0/5 | 0/5 | 0/5 | 0/5 | 0 |
| | Vaccine X2 | 0/5 | 0/5 | 0/5 | 0/5 | 0 |
| | Vaccine X4 | 0/5 | 0/5 | 0/5 | 0/5 | 0 |
| Comparative Immunized Groups | Vaccine g | 5/5 | 5/5 | 5/5 | 5/5 | 3 |
| | Vaccine h | 3/5 | 3/5 | 3/5 | 3/5 | 2 |
| | Vaccine i | 5/5 | 5/5 | 4/5 | 5/5 | 1 |
| | Vaccine Y2 | 5/5 | 5/5 | 5/5 | 5/5 | 2 |
| Control Group | — | 0/5 | 0/5 | 0/5 | 0/5 | 0 |

[1]Clinical Symptom;
[2]Body temperature
[3](number of animals on which any abnormality was recognized)/(number of animals tested).

Results of the efficacies of the vaccines are summarized in Tables 2-1 and 2-2. In the groups, into which the vaccines a, c or X2 had been injected, among the immunized groups, the CF-antibody titer began to increase after 4 week from the vaccine-injection and there was observed good antibody-response (1:128 to 1:256) after 8 weeks from the vaccine-injection, which was almost identical to that observed for the comparative immunized groups, into which the vaccine g had been injected, as the control and was obviously higher than that observed for the vaccine h-injected group. The vaccines d, f and X4 which were the water-in-oil-in-water type oil adjuvant vaccines of the present invention could be in good emulsions and exhibited good antibody-responses almost identical to that observed for the aforementioned water-in-oil emulsion type oil adjuvant vaccine. The vaccines i and Y2 prepared above and used in the comparative immunized groups as the controls were in unstable emulsions and these vaccine-injected groups distinctly exhibited an antibody response lower than that observed for those injected with the vaccines d and f.

The foregoing results clearly prove that the oil adjuvant vaccine of the present invention shows an immunopotentiating effect approximately identical to that observed for the non-metabolizable mineral oil-containing vaccines even when the former comprises only a metabolizable oil and that the former is excellent in the local reactivity as compared with the mineral oil-containing vaccines.

Moreover, these results also demonstrate that the oil adjuvant vaccine prepared by the method of the present invention has high stability even when it comprises only a metabolizable oil, that the vaccine exhibits an immunization effect approximately identical to that achieved by the conventional oil adjuvant vaccines comprising only non-metabolizable mineral oils, over a long period of time and that the former is excellent in the local reactivity as compared with the conventional vaccines comprising only mineral oils.

TABLE 2-1

Efficacy of Inactivated Vaccine for Swine Actinobacillus Infectious Disease

| Test Group | Vaccine | Time Elapsed after injection (week) | | | |
|---|---|---|---|---|---|
| | | 0 | 4 | 6 | 8 |
| Immunized Groups | vaccine a | <4[1] | 14 | 56 | 147 |
| | vaccine c | <4 | 18 | 111 | 169 |
| | vaccine d | <4 | 12 | 42 | 84 |
| | vaccine f | <4 | 11 | 37 | 74 |
| Comparative Immunized Groups | vaccine g | <4 | 37 | 97 | 111 |
| | vaccine h | <4 | <4 | 4 | 4 |
| | vaccine i | <4 | <4 | 4 | <4 |
| Control Group | — | <4 | <4 | <4 | <4 |

[1]Geometric mean of reciprocal of highest dilution showing ≧50% fixation, using App (type 2).

TABLE 2-2

Efficacy of Inactivated Vaccine for Swine Actinobacillus Infectious Disease

| Test Group | Vaccine | Time Elapsed after Injection (week) | | | | | |
|---|---|---|---|---|---|---|---|
| | | 0 | 4 | 6 | 8 | 12 | 16 |
| Immunized Groups | vaccine X2 | <4[1] | 24 | 147 | 169 | 147 | 74 |
| | vaccine X4 | <4 | 32 | 111 | 97 | 97 | 42 |
| Comp. Immunized Groups | vaccine g | <4 | 37 | 97 | 111 | 128 | 84 |
| | vaccine Y2 | <4 | <4 | 4 | 4 | <4 | <4 |
| Control Group | — | <4 | <4 | <4 | <4 | <4 | <4 |

[1]Geometric mean of reciprocal of highest dilution showing ≧50% fixation, using App (type 2).

Test Example 2
Inactivated Vaccine for Japanese Encephalitis

Japanese encephalitis virus (JEV) Nakayama strain was inoculated into a mouse brain, followed by cultivation thereof and harvesting the brain at an instance when the virus extremely proliferated. A homogenated brain was prepared, followed by precipitation thereof through centrifugation and inactivation of the resulting supernatant with formalin. The resulting supernatant was used as an antigen. As the aqueous phase, there was used a phosphate buffered saline to which formalin was added and whose virus content prior to the inactivation was adjusted to $10^{6.0}LD_{50}$/dose. With regard to immunized groups (each group comprised five 10-week-old SPF swines), 1 ml/swine of the vaccine b or 2 ml/swine of the vaccine e was intramuscularly injected. While 1 ml/swine of the vaccine g was intramuscularly injected into each swine belonging to comparative immunized groups (each group comprised five 10-week-old SPF swines). moreover, non-immunized control group comprised five swines and the control group was domiciled with either of the immunized groups. Each animal was inspected for the clinical symptoms including the observation of the site of injection for 2 weeks after the vaccination, the serum of each animal was collected at proper intervals throughout the test period and the sera were inspected for the antibody titer as determined by the hemagglutination inhibition (HI) test. The site of injection was examined by autopsy after 16 weeks from the vaccine-injection to thus determine the size and distribution of nodules formed which were evaluated on the basis of the lesion score (none: 0; ~severe: 3), followed by calculation of the average of 5 animals in each group.

The results of safety are listed in Table 3. The immunized groups and comparative immunized groups did not become feverish and did not show any abnormality in the clinical symptoms. In the autopsy after 16 weeks from the vaccine-injection, any particular lesion was not observed for the immunized groups, but there were observed nodules which would be formed due to the injected substances for the comparative immunized groups.

TABLE 3

Safety of Inactivated Vaccine for Japanese Encephalitis

| Test Group | Vaccine | Results C.S.[1] | B.T.[2] | Lesion Score |
|---|---|---|---|---|
| Immunized Groups | Vaccine b | 0/5[3] | 0/5[3] | 0 |
| | Vaccine e | 0/5 | 0/5 | 0 |
| Comp. Immunized Group | Vaccine g | 0/5 | 0/5 | 2.6 |
| Contol Group | — | 0/5 | 0/5 | 0 |

[1]Clinical Symptom;
[2]Body temperature
[3](number of animals on which any abnormality was recognized)/(number of animals tested).

Results on the inspection of the vaccines for the efficacy are summarized in Table 4. In the groups, into which the vaccine b had been injected, the HI-antibody titer began to increase after 4 week from the vaccine-injection and there was observed good antibody-response (1:80 to 1:160) after 8 weeks from the vaccine-injection, which was almost identical to that observed for the comparative immunized groups, into which the vaccine g had been injected, as the control. The vaccine e which was the water-in-oil-in-water type oil adjuvant vaccine of the present invention could be in good emulsions and increase the HI-antibody titer through only a single injection thereof, and showed an antibody-response almost identical to that observed for the aforementioned water-in-oil emulsion type oil adjuvant vaccine.

TABLE 4

Efficacy of Inactivated Vaccine for Japanese Encephalitis

| | | Time Elapsed After Injection (week) | | | |
|---|---|---|---|---|---|
| Test Group | Vaccine | 0 | 4 | 6 | 8 |
| Immunized Groups | vaccine b | <10[1] | 61 | 80 | 139 |
| | vaccine e | <10 | 92 | 92 | 92 |

TABLE 4-continued

Efficacy of Inactivated Vaccine for Japanese Encephalitis

| | | Time Elapsed After Injection (week) | | | |
|---|---|---|---|---|---|
| Test Group | Vaccine | 0 | 4 | 6 | 8 |
| Comp. Immunized Group | vaccine g | <10 | 70 | 92 | 92 |
| Control Group | — | | <10 | <10 | <10 | <10 |

[1]Reciprocal of hemagglutination-inhibition geometric mean titer.

The foregoing results clearly indicate that the oil adjuvant vaccine of the present invention exhibits an immunization effect almost identical to that observed for the non-metabolizable oil even when JEV is used as the antigen and that the former is excellent in the local reactivity as compared with the latter.

Test Example 3

Inactivated Vaccine for Newcastle Disease (ND)

Newcastle disease virus Ishii strain was inoculated ($10^{5.0}$ $EID_{50}$/egg) into allantoic cavity of 10-day-old embryonated eggs followed by cultivation at 37° C. for 4 days and collection of the allantoic fluid. The fluid was inactivated with an aqueous solution of formalin and used as the antigen. As the aqueous phase, there was used a phosphate buffered saline to which formalin was added and whose virus content prior to the inactivation was adjusted to $10^{8.0}EID_{50}$/dose.

As for immunized groups (each group comprised ten 5-week-old SPF chickens), 0.5 ml/chicken of the vaccine a or b, or 1 ml/chicken of the vaccine d or e was intramuscularly injected, and as for other immunized groups (each group comprised twenty 5-week-old SPF chickens), 0.5 ml/chicken of the vaccine X1 or X2, or 1.5 ml/chicken of the vaccine X5 was intramuscularly injected. As for comparative immunized groups (each group comprised ten 5-week-old SPF chickens), 0.5 ml/chicken of the vaccine g or 1 ml/chicken of the vaccine i was intramuscularly injected, and as for other comparative immunized groups (comprised twenty 5-week-old SPF chickens), 0.5 ml/chicken of the vaccine Y2 was intramuscularly injected. Moreover, non-immunized control groups each comprised ten or twenty chickens were domiciled with the immunized groups each comprised ten or twenty chickens, respectively.

As for the vaccines a, b, d and e, each animal was inspected for the clinical symptoms including the observation of the injection site for 10 weeks after the vaccination, the serum of each animal was collected after 10 weeks from the vaccination and the sera were inspected for the hemagglutination inhibition (HI) antibody titer. The site of injection was examined by autopsy (5 animals per group) after 10 weeks from the vaccination to thus determine the degree and distribution of residues which were evaluated on the basis of the lesion score (none: 0; ~severe: 3), followed by calculation of the average for each group. The remaining 5 animals in each group were challenged by intramuscularly injecting ND virus Sato strain in an amount of $10^4$ MLD (Minimum Lethal Dose)/chicken followed by observation of the clinical symptoms over 2 weeks after the challenge and simultaneous collection of blood samples after 2 weeks from the challenge, inspection of the collected blood for the HI antibody titer to thus determine whether the animals were infected with the virus or not.

As for the vaccines X1, X2, X5 and Y2, each animal was inspected for the clinical symptoms including the observation of the injection site for 20 weeks after the vaccination, the serum of each animal was collected and inspected for the hemagglutination inhibition (HI) antibody titer. The site of injection was examined by autopsy (10 animals per group) after 10 weeks from the vaccination to thus determine the degree and distribution of residues which were evaluated on the basis of the lesion score (none: 0; ~severe: 3), followed by calculation of the average for each group. The remaining 10 animals in each group were challenged by intramuscularly injecting ND virus Sato strain in an amount of $10^4$ MLD (Minimum Lethal Dose)/chicken after 20 weeks from the injection followed by observation of the clinical symptoms over 2 weeks after the challenge and simultaneous collection of blood samples after 2 weeks from the challenge, inspection of the collected blood for the HI antibody titer to thus determine whether the animals were infected with the virus or not.

The results of safety are listed in Tables 5-1 and 5-2. The comparative immunized groups into which the vaccines g, i and Y2 were injected transiently became claudication immediately after the vaccination. On the other hand, all of the immunized groups into which the vaccines of this invention had been injected did not show any abnormality through the testing period. In the autopsy after 10 weeks from the vaccination, there was observed a small amount of an oily substance in two out of five animals belonging to the group into which the vaccine b had been injected, in three out of five belonging to the group into which the vaccine X2 had been injected, but there was not any lesion in the other immunized groups. In all of the comparative immunized groups into which the vaccines g, i and Y2 were injected, however, there were observed the presence of from medium to severe residues.

the immunized groups which were water-in-oil type oil adjuvant vaccines with those observed for the vaccine g injected into the comparative immunized group, there was not observed any difference therebetween and thus they were considered to be identical to one another. On the other hand, when comparing the results observed for the vaccines d, e and X5 injected into the immunized groups which were water-in-oil-in-water type oil adjuvant vaccines with those observed for the vaccines i and Y2 injected into the comparative immunized groups, the HI-antibody titers observed for the latter were distinctly lower than those observed for the former.

The foregoing results clearly prove that the oil adjuvant vaccine of the present invention shows an immunization effect approximately identical to that observed for the non-metabolizable mineral oil-containing vaccines even when the former comprises only a metabolizable oil and that the former is considerably excellent in the local reactivity as compared with the mineral oil-containing oil adjuvant vaccines.

Moreover, these results also demonstrate that the oil adjuvant vaccine prepared by the method of the present invention has high stability, that the vaccine exhibits an immunization effect approximately identical to that achieved by the conventional oil adjuvant vaccines comprising only non-metabolizable mineral oils and that the former is excellent in the local reactivity as compared with the conventional oil adjuvant vaccines. In addition, they also prove that the water-in-oil-in-water type oil adjuvant vaccine prepared by the present invention likewise has high

TABLE 5-1

Safety of Inactivated Vaccine for Newcastle Disease

| Test Group | Vaccine | Time Elapsed after Injection | | | | | | Lesion Score |
|---|---|---|---|---|---|---|---|---|
| | | 0 | 2 | 3 | 4 | 6 | 10 | |
| Immunized Groups | Vaccine a | 0/10[1] | 0/10 | 0/10 | 0/10 | 0/10 | 0/10 | 0 |
| | Vaccine b | 0/10 | 0/10 | 0/10 | 0/10 | 0/10 | 0/10 | 0.4 |
| | Vaccine d | 0/10 | 0/10 | 0/10 | 0/10 | 0/10 | 0/10 | 0 |
| | Vaccine e | 0/10 | 0/10 | 0/10 | 0/10 | 0/10 | 0/10 | 0 |
| Comp. Immunized Groups | Vaccine g | 6/10 | 0/10 | 0/10 | 0/10 | 0/10 | 0/10 | 2.2 |
| | Vaccine i | 4/10 | 0/10 | 0/10 | 0/10 | 0/10 | 0/10 | 1.8 |
| Control Group | — | 0/10 | 0/10 | 0/10 | 0/10 | 0/10 | 0/10 | 0 |

[1](number of animals on which any abnormality was recognized)/(number of animals tested).

TABLE 5-2

Safety of Inactivated Vaccine for Newcastle Disease

| Test Group | Vaccine | Time Elapsed after Injection | | | | | | | | | Lesion Score |
|---|---|---|---|---|---|---|---|---|---|---|---|
| | | 0 | 2 | 3 | 4 | 6 | 8 | 12 | 16 | 20 | |
| Immunized Groups | Vaccine X1 | 0/20[1] | 0/20 | 0/20 | 0/20 | 0/20 | 0/20 | 0/10 | 0/10 | 0/10 | 0 |
| | Vaccine X2 | 0/20 | 0/20 | 0/20 | 0/20 | 0/20 | 0/20 | 0/10 | 0/10 | 0/10 | 0.6 |
| | Vaccine X5 | 0/20 | 0/20 | 0/20 | 0/20 | 0/20 | 0/20 | 0/10 | 0/10 | 0/10 | 0 |
| Comp. Immunized Group | Vaccine Y2 | 9/20 | 0/20 | 0/20 | 0/20 | 0/20 | 0/20 | 0/10 | 0/10 | 0/10 | 1.8 |
| Control Group | — | 0/20 | 0/20 | 0/20 | 0/20 | 0/20 | 0/20 | 0/10 | 0/10 | 0/10 | 0 |

[1](number of animals on which any abnormality was recognized)/(number of animals tested).

Results on the inspection of the vaccines for the efficacy are summarized in Tables 6-1 and 6-2. When comparing the results observed for the vaccines a, b, X1 and X2 injected to stability and shows excellent efficacy over a long period of time while it is also excellent in the local reactivity.

TABLE 6-1

Efficacy of Inactivated Vaccine for Newcastle Disease

| Test Group | Vaccine | Time Elapsed after Injection | | Livability |
| --- | --- | --- | --- | --- |
| | | 0 week | 10 weeks | (%)[2] |
| Immunized Groups | vaccine a | <5[1] | 520 | 100 |
| | vaccine b | <5 | 453 | 100 |
| | vaccine d | <5 | 422 | 100 |
| | vaccine e | <5 | 394 | 100 |
| Comp. Immunized Groups | vaccine g | <5 | 597 | 100 |
| | vaccine i | <5 | 171 | 100 |
| Control Group | — | <5 | <5 | 0 |

[1]Reciprocal of hemagglutination-inhibition geometric mean titer.
[2](number of asymptomatic allowable animals)/(number of total animals tested).

TABLE 6-2

Efficacy of Inactivated Vaccine for Newcastle Disease

| Test Group | Vaccine | Time After Injection (week) | | | | Livability |
| --- | --- | --- | --- | --- | --- | --- |
| | | 0 | 10 | 15 | 20 | (%)[2] |
| Immunized Groups | vaccine X1 | <5[1] | 557 | 520 | 453 | 100 |
| | vaccine X2 | <5 | 640 | 485 | 520 | 100 |
| | vaccine X5 | <5 | 597 | 422 | 368 | 100 |
| Comp. Immunized Group | vaccine Y2 | <5 | 171 | 8 | <5 | 100 |
| Control Group | — | <5 | <5 | <5 | <5 | 0 |

[1]Reciprocal of hemagglutination-inhibition geometric mean titer.
[2](number of asymptomatic allowable animals)/(number of total animals tested).

Test Example 4
Inactivated Vaccine for Bovine Ephemeral Fever

HmLu-1 cells formed into a monolayer of the cells was inoculated with bovine ephemeral fever (BEF) virus YHL strain so that MOT (Multiplicity of infection) was set at 0.01, followed by adsorbing the virus onto the layer at 37° C. for 60 minutes, then cultivation thereof at 34° C. for 3 days to add a medium and inactivation of the supernatant with formalin. As the aqueous phase, there was used a phosphate buffered saline to which formalin was added and whose virus content prior to the inactivation was adjusted to $10^{6.0}TCID_{50}$/dose.

Regarding immunized groups (each group comprised two bovines each having a body weight of about 150 kg), 1 ml/bovine of the vaccine a, X1 or X3, or 3 ml/bovine of the vaccine d was intramuscularly injected, while 1 ml/bovine of the vaccine g or Y1 was intramuscularly injected into each bovine belonging to comparative immunized groups (each group comprised two bovines having a body weight of 150 kg). Moreover, non-immunized control group comprised two bovines and the control group were domiciled with one of the immunized groups. Each animal was inspected for the clinical symptoms including the observation of the site of injection and the body temperature thereof over 2 weeks after the vaccination. Moreover, the serum of each animal was collected at constant intervals after the vaccine-injection and the sera were inspected for the neutralizing antibody titer. The site of injection was examined by autopsy after 20 weeks from the vaccine-injection.

The results of safety are listed in Table 7. The immunized groups and the comparative immunized groups did not show any abnormality in the clinical symptom and body temperature. In the autopsy of the vaccine-injected sites, the vaccine remaining in the sites was observed for only the comparative immunized groups.

TABLE 7

Safety of Inactivated Vaccine for Bovine Ephemeral Fever

| Test Group | Vaccine | Results | | Lesion Score |
| --- | --- | --- | --- | --- |
| | | C.S.[1] | B.T.[2] | |
| Immunized Groups | Vaccine a | 0/2[3] | 0/2[3] | 0 |
| | Vaccine d | 0/2 | 0/2 | 0 |
| | Vaccine X1 | 0/2[3] | 0/2[3] | 0 |
| | Vaccine X3 | 0/2 | 0/2 | 0 |
| Comp. Immunized Groups | Vaccine g | 0/2 | 0/2 | 1 |
| | Vaccine Y1 | 0/2 | 0/2 | 0 |
| Control Group | — | 0/2 | 0/2 | 0 |

[1]Clinical Symptom;
[2]Body temperature
[3](number of animals on which any abnormality was recognized)/(number of animals tested).

Results on the inspection of the vaccines for the efficacy are summarized in Tables 8-1 and 8-2. The antibody titers of the immunized groups began to increase after 4 week from the vaccination and showed a change in the antibody titer identical to that observed for the comparative immunized groups, the immunized groups into which the vaccines X1 and X3 had been injected showed changes in the antibody titers superior to those observed for the comparative immunized group into which the vaccine Y1 had been injected and this tendency was maintained up to 20 weeks after the vaccination.

TABLE 8-1

Efficacy of Inactivated Vaccine for Bovine Ephemeral Fever

| Test Group | Vaccine | Time Elapsed After Injection (week) | | | |
| --- | --- | --- | --- | --- | --- |
| | | 0 | 4 | 6 | 8 |
| Immunized Groups | vaccine a | <2[1] | 16 | 32 | 32 |
| | | <2 | 32 | 64 | 64 |
| | vaccine d | <2 | 32 | 32 | 32 |
| | | <2 | 64 | 32 | 32 |
| Comp. Immunized Group | vaccine g | <2 | 32 | 64 | 32 |
| | | <2 | 32 | 64 | 64 |
| Control Group | — | <2 | <2 | <2 | <2 |
| | — | <2 | <2 | <2 | <2 |

[1]BEF neutralizing antibody titer.

TABLE 8-2

Efficacy of Inactivated Vaccine for Bovine Ephemeral Fever

| Test Group | Vaccine | Time Elapsed After Injection (week) | | | | | |
| --- | --- | --- | --- | --- | --- | --- | --- |
| | | 0 | 4 | 6 | 8 | 12 | 16 | 20 |
| Immunized Groups | vaccine X1 | <2[1] | 8 | 16 | 32 | 32 | 32 | 32 |
| | vaccine X1 | <2 | 32 | 32 | 64 | 64 | 64 | 64 |
| | vaccine X3 | <2 | 32 | 32 | 32 | 32 | 32 | 32 |
| | vaccine X3 | <2 | 32 | 64 | 64 | 64 | 32 | 32 |
| Comp. Immunized Groups | vaccine Y1 | <2 | 8 | 8 | 4 | 4 | 4 | 4 |
| | vaccine Y1 | <2 | 16 | 8 | 8 | 8 | 8 | 8 |
| Control Group | — | <2 | <2 | <2 | <2 | <2 | <2 | <2 |
| | | <2 | <2 | <2 | <2 | <2 | <2 | <2 |

[1]BEF neutralizing antibody titer.

The foregoing results clearly indicate that the oil adjuvant vaccine of the present invention exhibits an immunization effect almost identical to that observed for a non-metabolizable mineral oil even when the oil adjuvant vaccine of the present invention comprised only a metabolizable oil and that the former is considerably excellent in the local reactivity as compared with the mineral oil-containing adjuvant vaccine.

These results also prove that the oil adjuvant vaccine prepared by the method of the present invention has high stability, shows an immunization effect over a long period of time and is also excellent in the local reactivity.

Stability

Then the oil adjuvant vaccines prepared in Examples 4 to 6 and 7 to 11 and Comparative Examples 4 to 5 were inspected for their stability immediately after the preparation thereof according to the following procedures. These results are summarized in the following Table 9.

Test Example 5
Water-in-Oil Type Adjuvant Vaccine

Each water-in-oil type oil adjuvant vaccine (5 ml) was put into a 15 ml volume polypropylene Spitz tube (sterilized) equipped with a cap to thus evaluate the stability thereof under various temperature conditions. Each tube was visually observed after one day, 3 months and 12 months from the preparation, followed by observation of each sample using a phase-contrast microscope (magnification:×1000) (5 visual fields each) and the results thus obtained were evaluated on the basis of the following evaluation criteria:

⊚: No (or little) phase separation and no (or little) change of the droplets'size were observed.

○: Slightly separation of the oil phase only, and/or slightly change of the droplets' size was observed.

△: Separation of the aqueous phase was observed, and/or "breaking*" of the droplets was observed partially.

X: Separation of both the oil phase and the aqueous phase was observed, and/or "breaking*" of the droplets was observed clearly.

X X: The phase separation was observed clearly, and/or the antigen in the internal phase was hardly held.

*) "Breaking" is the spontaneous joining of small droplets in the emulsion to form larger ones (coalescence).

Test Example 6
Water-in-Oil-in-Water Type Oil Adjuvant Vaccine

Each water-in-oil-in-water type oil adjuvant vaccine (10 ml) was introduced into a 20 ml volume glass screw tube (sterilized) equipped with a cap to thus evaluate the stability thereof under various temperature conditions. Each tube was visually observed after one day, 3 months and 12 months from the preparation, followed by observation of each sample using a phase-contrast microscope (magnification:× 1000) (5 visual fields each) and the results thus obtained were evaluated on the basis of the following evaluation criteria:

⊚: No (or little) phase separation and no (or little) change of the droplets'size were observed.

○: Slightly change of the droplets' size was observed, but the water-in-oil-in-water form remained.

△: Coalescence of the droplets was observed clearly, but the water-in-oil-in-water form remained.

X: "Breaking" of the droplets was observed clearly such that the water-in-oil-in-water form didn't remain satisfactory.

X X: The water-in-oil-in-water form broke almost, and the phase separation was observed clearly.

※ "Breaking" is the spontaneous joining of small droplets in the emulsion to form larger ones (coalescence).

TABLE 9

Stability of Oil Adjuvant Vaccine

| Vaccine No. | Storage at 4° C. (month) | | | Storage at Ord. Temp. (month) | | |
|---|---|---|---|---|---|---|
| | 1(day) | 3 | 12 | 1(day) | 3 | 12 |
| X1 | ⊚ | ⊚ | ⊚ | ⊚ | ⊚ | ⊚ |
| X2 | ⊚ | ⊚ | ⊚ | ⊚ | ⊚ | ⊚ |
| X3 | ⊚ | ⊚ | ⊚ | ⊚ | ⊚ | ⊚ |
| X4 | ⊚ | ⊚ | ⊚ | ⊚ | ⊚ | ⊚ |
| X5 | ⊚ | ⊚ | ⊚ | ⊚ | ⊚ | ⊚ |
| Y1 | ⊚ | ○ | △ | ⊚ | ○ | X |
| Y2 | ○ | X | XX | ○ | X | XX |

The results listed in Tables 1 to 9 clearly indicate that oil adjuvant vaccines excellent in both safety and ability to induce an antibody-production can be prepared by the present invention, that oil adjuvant vaccines which have low viscosities and are excellent in both long-term stability and sustained ability to induce an antibody-production can be prepared by the method which comprises the steps of adding, to an oil component, a polyoxyethylene hydroxy fatty acid triglyceride and a gel-like substance comprising an aqueous solution of the components B and E of the present invention, mixing these ingredients and then adding an aqueous phase which contains a biologically acceptable and effective amount of antigens to thus emulsify the aqueous phase in the oil phase, and that a water-in-oil-in-water type oil adjuvant vaccine excellent in both safety and antibody-producing avility can be obtained by the method comprising the step of adding the water-in-oil type oil adjuvant vaccine prepared by the foregoing method to an aqueous phase containing the mixed emulsifying agent of the present invention to thus again emulsify the vaccine into the aqueous phase.

Effects of the Invention

As has been discussed above in detail, the present invention permits the preparation of useful oil adjuvant vaccines which show a high ability to induce an antibody-production over a long period of time without using, in pharmaceuticals, any immunostimulator such as vegetable lectins, and are excellent in requirements for medicines such as stability and safety.

What is claimed is:

1. A water-in-oil type oil adjuvant vaccine comprising 20 to 90% by weight of an oil phase A) which is in a liquid state at ordinary temperature; 0.5 to 30% by weight of an emulsifying agent comprising a non-ionic surfactant B) which is a partial ester derived from a polyhydric alcohol carrying at least three hydroxyl groups and a fatty acid and which is in a liquid state at 40° C. and a hydroxy fatty acid triglyceride C) wherein a hydroxy group of the fatty acid is polyoxyethylenated with 20 to 60 ethylene oxide units; E) 0.01 to 10% by weight of an amino acid or a salt thereof and 0.01 to 10% by weight of a non-reducing sugar or a sugar alcohol having at least 5 hydroxyl groups in the molecule; and 5 to 75% by weight of an aqueous phase D) containing a biologically acceptable and effective amount of antigens.

2. A water-in-oil-in-water type oil adjuvant vaccine comprising a water-in-oil type oil adjuvant phase comprising 30 to 90% by weight of an oil phase A) which is in a liquid state at ordinary temperature, 0.5 to 30% by weight of an emulsifying agent comprising a non-ionic surfactant B) which is a partial ester derived from a polyhydric alcohol carrying at least three hydroxyl groups and a fatty acid and which is in a liquid state at 40° C. and a hydroxy fatty acid triglyceride C) wherein a hydroxy group of the fatty acid is polyoxyethylenated with 20 to 60 ethylene oxide units, E) 0.01 to 10% by weight of an amino acid or a salt thereof and 0.01 to 10% by weight of a non-reducing sugar or a sugar alcohol having at least 5 hydroxyl groups in the molecule and 5 to 65% by weight of an aqueous phase D) containing a biologically acceptable and effective amount of antigens; and an outer aqueous phase F) comprising 0.2 to 20% by weight of an emulsifying agent which comprises a non-ionic surfactant, wherein the non-ionic surfactant has an HLB value of not less than 10.

3. The oil adjuvant vaccine as set forth in claim 1 or 2, wherein the oil phase A) which is in a liquid state at ordinary temperature is an ester type oil.

4. The oil adjuvant vaccine as set forth in claim 1 or 2, wherein the oil phase A) which is in a liquid state at ordinary temperature is a mixture of an ester type oil and squalene.

5. The oil adjuvant vaccine as set forth in claim 1 or 2 wherein the oil phase A) which is in a liquid state at ordinary temperature is an ester derived from a fatty acid which comprises not less than 85% by weight of cis-Δ9-octadecenoic acid and not less than 90% by weight of cis-Δ9-alkenoic acids, and an alcohol.

6. The oil adjuvant vaccine as set forth in claim 1, or 2, wherein the partial ester is derived from a polyhydric alcohol carrying at least three hydroxy groups and a fatty acid which comprises not less than 85% by weight of cis-Δ9-octadecenoic acid and not less than 90% by weight of cis-Δ9-alkenoic acids.

7. The oil adjuvant vaccine of claim 2, wherein the outer aqueous phase F) is an outer aqueous phase comprising 0.2 to 20% by weight of a mixture comprising a glycerophospholipid and a non-ionic surfactant, wherein the non-ionic surfactant has an HLB value of not less than 10.

8. A method for preparing a water-in-oil type oil adjuvant vaccine as set forth in claim 1 comprising the steps of adding, to an oil phase A) which is in a liquid state at ordinary temperature, a non-ionic surfactant B) which is a partial ester derived from a polyhydric alcohol carrying at least three hydroxyl groups and a fatty acid and which is in a liquid state at 40° C., a hydroxy fatty acid triglyceride C) wherein a hydroxy group of the fatty acid is polyoxyethylenated with 20 to 60 ethylene oxide units, and a product obtained by admixing and emulsifying the non-ionic surfactant B) and an aqueous solution containing E) an amino acid or a salt thereof and a non-reducing sugar or a sugar alcohol having at least 5 hydroxyl groups the molecule, in a weight ratio: the non-ionic surfactant B) the aqueous solution of the component E) ranging from 1:1 to 20; and then adding an aqueous phase D) containing biologically acceptable and effective amount of antigens to thus emulsify the aqueous phase in the oil phase.

9. A method for preparing a water-in-oil-in-water type oil adjuvant vaccine as set forth in claim 2 comprising the steps of adding, to an oil phase A) which is in a liquid state at ordinary temperature, a non-ionic surfactant B) which is a partial ester derived from a polyhydric alcohol carrying at least three hydroxyl groups and a fatty acid and which is in a liquid state at 40° C., a hydroxy fatty acid triglyceride C) wherein a hydroxy group of the fatty acid is polyoxyethylenated with 20 to 60 ethylene oxide units, and a product obtained by admixing and emulsifying the non-ionic surfactant B) and an aqueous solution containing E) an amino acid or a salt thereof and a non-reducing sugar or a sugar alcohol having at least 5 hydroxyl groups in the molecule, in a weight ratio: the non-ionic surfactant B) to the aqueous solution of the component E) ranging from 1:1 to 1:20; then adding an aqueous phase D) containing a biologically acceptable and effective amount of antigens to thus form a water-in-oil type oil adjuvant vaccine; and adding the water-in-oil type oil adjuvant vaccine to an aqueous phase F) containing 0.2 to 20% by weight of an emulsifying agent which comprises a non-ionic surfactant, wherein the non-ionic surfactant has an HLB value of not less than 10, to thus emulsify the water-in-oil type adjuvant vaccine into the aqueous phase.

* * * * *